United States Patent [19]

Hirota et al.

[11] Patent Number: 5,096,891
[45] Date of Patent: Mar. 17, 1992

[54] CYCLIC AMP DERIVATIVE OINTMENTS

[75] Inventors: Sadao Hirota; Hitoshi Yamauchi, both of Tokyo, Japan

[73] Assignee: Daiichi Seiyaku Co., Ltd., Tokyo, Japan

[21] Appl. No.: 330,580

[22] Filed: Mar. 30, 1989

[30] Foreign Application Priority Data

Mar. 30, 1988 [JP] Japan .................................. 63-77915

[51] Int. Cl.⁵ ...................... A61K 31/70; C07H 19/06; C07H 19/16
[52] U.S. Cl. ......................................... 514/47; 514/58; 514/59; 514/925; 514/928; 514/969; 514/970
[58] Field of Search ...................... 514/47, 58, 59, 925, 514/928, 969, 970

[56] References Cited

U.S. PATENT DOCUMENTS

| | | | |
|---|---|---|---|
| 3,978,213 | 8/1976 | Lapin et al. | 514/47 |
| 4,005,191 | 1/1977 | Clark | 424/687 |
| 4,271,144 | 6/1981 | Holly | 514/59 |
| 4,352,794 | 10/1982 | Koch | 514/58 |
| 4,478,995 | 10/1984 | Shinoda et al. | 514/925 |
| 4,481,197 | 11/1984 | Rideout et al. | 514/47 |
| 4,537,767 | 8/1985 | Rothman et al. | 514/59 |
| 4,791,103 | 12/1988 | Triuedi et al. | 514/47 |
| 4,793,998 | 12/1988 | Murthy et al. | 514/970 |
| 4,803,213 | 2/1989 | Iida et al. | 514/970 |
| 4,806,524 | 2/1989 | Kawaguchi et al. | 514/970 |

FOREIGN PATENT DOCUMENTS 0248740 12/1987 European Pat. Off. .
249873 12/1987 European Pat. Off. .
2358155 2/1978 France .

*Primary Examiner*—Ronald W. Griffin
*Attorney, Agent, or Firm*—Sughrue, Mion, Zinn, Macpeak & Seas

[57] ABSTRACT

An ointment comprising an adenosine 3',5'-cyclic phosphate derivative as an active ingredient, an ointment base having water-absorbing and drying properties, a saccharide and/or inorganic high polymer is disclosed. The ointment exhibits improved stability of the adenosine 3',5'-cyclic phosphate derivative.

5 Claims, No Drawings

CYCLIC AMP DERIVATIVE OINTMENTS

FIELD OF THE INVENTION

This invention relates to an ointment containing an adenosine 3',5'-cyclic phosphate derivative as an active ingredient.

BACKGROUND OF THE INVENTION

Conventional pharmaceutical preparations for treatment of various skin ulcers include ointments containing antibiotics, antibacterial agents, or enzymes; skin lotions; water-absorbing powders of high polymers; wound protectives; and the like. For particular use in the treatment of skin ulcers with exudate, ointments having water-absorbing and drying properties are commonly employed.

On the other hand, therapeutic effects of adenosine 3',5'-cyclic phosphate (hereinafter referred to as cyclic AMP) derivatives on various skin ulcers have been elucidated as disclosed in JP-A-63-107935 (the term "JP-A" as used herein means an "unexamined published Japanese patent application").

Ointment bases which are believed most effective for the preparations of the cyclic AMP derivatives in the treatment of skin ulcers are of the type having water-absorbing and drying properties. However, these ointment bases contain therein a trace amount of water. If the cyclic AMP derivative is dispersed or dissolved in such ointment bases, the cyclic AMP derivatives are gradually hydrolyzed, thus becoming ineffective through long-term preservation.

SUMMARY OF THE INVENTION

The present inventors conducted extensive investigations for stabilizing the cyclic AMP derivatives in ointments containing the ointment base having water-absorbing and drying properties. As a result, it has now been found that the use of saccharides and/or inorganic high polymers stabilizes the cyclic AMP derivatives in the ointment to sustain its effectiveness. The present invention has been completed based on this finding.

That is, the present invention relates to an ointment comprising a cyclic AMP derivative as an active ingredient, an ointment base having water-absorbing and drying properties, a saccharide and/or an inorganic high polymer.

DETAILED DESCRIPTION OF THE INVENTION

The cyclic AMP derivative which can be used in the present invention includes sodium $N^6,2'$-O-dibutyryladenosine 3',5'-cyclic phosphate (hereinafter referred to as DBcAMP), sodium 2'-O-butyryladenosine 3',5'-cyclic phosphate (hereinafter referred to as 2'-O-MBcAMP), sodium $N^6$-butyryladenosine 3',5'-cyclic phosphate (hereinafter referred to $N^6$-MBcAMP), sodium adenosine 3',5'-cyclic phosphate (hereinafter referred to as cAMP), 8-benzylthio-$N^6$-butyryladenosine 3',5'-cyclic phosphate (hereinafter referred to as BTBcAMP), 8-benzylthio-2'-O-butyryladenosine 3',5'-cyclic phosphate and 8-benzylthioadenosine 3',5'-cyclic phosphate (hereinafter referred to as BT-cAMP). These cyclic AMP derivatives may be used either independently or in combination of two or more thereof in the present invention.

The ointment base having water-absorbing and drying properties which can be used in the present invention includes polyoxy alcohols (e.g., polyethylene glycols of various molecular weights, glycerin, propylene glycol, butylene glycol, or a mixture thereof), mixtures of these polyoxy alcohols and higher alcohols (e.g., stearyl alcohol, cetyl alcohol), etc. A mixing ratio of the above mixtures is not particularly limited. Among them, preferred ointment bases are the polyethylene glycols and the mixture of two or more types thereof (differring in molecular weight), for example, an equal amount mixture of polyethylene glycol 400 and polyethylene glycol 4000.

The saccharides to be used in the ointment of the present invention include dextrin, dextran, $\alpha$-, $\beta$-, $\gamma$-cyclodextrin, a mixture thereof and the like. These saccharides are usually dispersed in the ointment base. The amount of the saccharide to be added is not particularly limited, but preferably ranges from about 0.5 to 20 parts, more preferably from 1 to 10 parts, per 100 parts of the ointment base by weight.

The inorganic high polymers in the ointment of the present invention include a dried aluminum hydroxide gel, synthetic magnesium silicate, hydrotalcite, a mixture thereof and the like. The inorganic high polymer is usually dispersed in the ointment base in an amount which is not limited, but preferably ranging from about 0.1 to 10 parts, more preferably from 0.5 to 2 parts, per 100 parts of the ointment base by weight.

The ointment according to the present invention can contain pharmaceutical additives, for example, a perfume, a coloring agent and a water-soluble polymer such as carboxymethyl cellulose, in addition to the above materials.

The ointment according to the present invention can be prepared according to a usual manner known for preparing ointments. In some detail, the ointment base is melted by heating, usually at a temperature of from about 60 to about 70° C., a saccharide and/or an inorganic high polymer is added thereto and thoroughly dispersed therein, and a prescribed amount of the cyclic AMP derivative is dissolved therein, followed by cooling to obtain the desired ointment.

The thus obtained ointment of the present invention exhibits excellent stability of the cyclic AMP derivative as compared with that in the conventional ointment prepared simply by dissolving the cyclic AMP derivative in the ointment base having water-absorbing and drying properties.

The present invention is now illustrated in greater detail by way of the following Control Example, Examples, and Test Example, but it should be understood that the present invention is not considered to be limited thereto.

CONTROL EXAMPLE

In a 100 ml beaker were put 57.35 g of polyethylene glycol 400 and 40 g of polyethylene glycol 4000 and melted at about 65° C. in a mantle heater. To the molten ointment base was added 2.65 g of DBcAMP, and the mixture was stirred in a homomixer (T.K. Homomixer, Model M) for 5 minutes to dissolve DBcAMP, followed by cooling to prepare 100 g of an ointment.

EXAMPLE 1

Polyethylene glycol 400 (56.1 g) and polyethylene glycol 4000 (40 g) were melted in the same manner as in Control Example, and 1.25 g of dextrin was added thereto. The mixture was thoroughly dispersed in a T.K. homomixer Model M for 5 minutes. Then, 2.65 g of DBcAMP was dissolved therein and cooled to prepare 100 g of an ointment.

EXAMPLE 2

An ointment containing DBcAMP was prepared in the same manner as in Example 1, except for using dextran T40 in place of dextrin.

EXAMPLE 3

Polyethylene glycol 400 (52 g) and polyethylene glycol 4000 (40 g) were melted in the same manner as in Control Example, and 5 g of β-cyclodextrin was added thereto and thoroughly dispersed in a T.K. homomixer Model M for 5 minutes. To the mixture was added 3 g of DBcAMP and dissolved, followed by cooling to prepare 100 g of an ointment.

EXAMPLE 4

Polyethylene glycol 600 (47 g) and polyethylene glycol 4000 (40 g) were melted in the same manner as in Control Example, and 10 g of dextrin was added thereto, followed by thoroughly dispersing in a T.K. homomixer Model M for 5 minutes. Three grams of DBcAMP was added and dissolved therein, followed by cooling to obtain 100 g of an ointment.

EXAMPLE 5

An ointment containing DBcAMP was prepared in the same manner as in Example 4, except for using 40 g of α-cyclodextrin in place of dextrin.

EXAMPLE 6

Polyethylene glycol 600 (56 g) and polyethylene glycol 4000 (40 g) were melted in the same manner as in Control Example, and 1 g of a dried aluminum hydroxide gel was added thereto. The mixture was thoroughly dispersed in a T.K. homomixer Model M for 5 minutes. Three grams of DBcAMP was dissolved therein and cooled to obtain 100 g of an ointment.

EXAMPLE 7

Polyethylene glycol 600 (56 g) and polyethylene glycol 4000 (30 g) were melted in the same manner as in Control Example, and 10 g of dextrin and 1 g of a dried aluminum hydroxide gel were added thereto, followed by thoroughly dispersing in a T.K. homomixer Model M for 5 minutes. Three grams of DBcAMP was then dissolved therein and cooled to prepare 100 g of an ointment.

EXAMPLE 8

Polyethylene glycol 400 (67 g) and polyethylene glycol 4000 (28 g) were melted in the same manner as in Control Example, and 1 g of dextrin and 1 g of a dried aluminum hydroxide gel were added thereto. The mixture was thoroughly dispersed in a T.K. homomixer Model M for 5 minutes. Then, 3 g of DBcAMP was dissolved therein and cooled to prepare 100 g of an ointment.

EXAMPLE 9

Polyethylene glycol 400 (67 g) and polyethylene glycol 4000 (26 g) were melted in the same manner as in Control Example, and 3 g of dextrin and 1 g of a dried aluminum hydroxide gel were added thereto. The mixture was thoroughly dispersed in a T.K. homomixer Model M for 5 minutes, and 3 g of DBcAMP was then dissolved therein, followed by cooling to prepare 100 g of an ointment.

TEST EXAMPLE

Each of the ointments prepared in Control Example and Examples 1 to 9 was put in a glass bottle and stored in a thermostat kept at 50° C. for 1 month. The residual DBcAMP content (% versus initial content) after storage of 1 month was determined by liquid chromatography, as described in Journal of Chromatography 238, 495 (1982). The results obtained are shown in Table 1 below.

TABLE 1

| Stability of DBcAMP on Storage for 1 Month (at 50° C.) | |
|---|---|
| Example No. | Residual DBcAMP (%) |
| Control Example | 51.5 |
| Example 1 | 72.0 |
| Example 2 | 71.0 |
| Example 3 | 76.9 |
| Example 4 | 80.4 |
| Example 5 | 79.6 |
| Example 6 | 81.8 |
| Example 7 | 85.8 |
| Example 8 | 78.2 |
| Example 9 | 77.0 |

As is apparent from Table 1, the stability of DBcAMP in each of the ointments prepared in Examples 1 to 9 was higher than that of Control Example. Therefore, it was confirmed that the stability of the cyclic AMP derivative in the ointment can be significantly improved by using saccharides and/or inorganic high polymers in combination with the ointment base having water-absorbing and drying properties.

While the invention has been described in detail and with reference to specific embodiments thereof, it will be apparent to one skilled in the art that various changes and modifications can be made therein without departing from the spirit and scope thereof.

What is claimed is:

1. An ointment comprising an adenosine 3',5'-cyclic phosphate derivative as an active ingredient, an ointment base having water-absorbing and drying properties, a saccharide, where the saccharide is dextrin, dextran, α-, β- or γ-cyclodextrin or a mixture thereof, and an inorganic high polymer, where the inorganic high polymer is a dried aluminum hydroxide gel, synthetic magnesium silicate, hydrotalcite or a mixture thereof.

2. An ointment as claimed in claim 1, wherein said adenosine 3',5'-cyclic phosphate derivative is sodium $N^6$,2'-O-dibutyryladenosine 3',5'-cyclic phosphate, sodium 2'-O-butyryladenosine 3',5'-cyclic phosphate, sodium $N^6$-butyryladenosine 3',5'-cyclic phosphate, sodium adenosine 3',5'-cyclic phosphate, 8-benzylthio-$N^6$-butyryladenosine 3',5'-cyclic phosphate, 8-benzylthio-2'-O-butyryladenosine 3',5'-cyclic phosphate or 8-benzylthioadenosine 3',5'-cyclic phosphate.

3. An ointment as claimed in claim 1, wherein said ointment base comprises two or more polyethylene glycols having different molecular weights.

4. An ointment as claimed in claim 1, wherein said saccharide is used in an amount of from about 0.5 to 20 parts per 100 parts of the ointment base by weight.

5. An ointment as claimed in claim 1, wherein said inorganic high polymer is used in an amount of from about 0.1 to 10 parts per 100 parts of the ointment base by weight.

* * * * *